US012721921B2

(12) United States Patent
Leonhard et al.

(10) Patent No.: US 12,721,921 B2
(45) Date of Patent: Sep. 1, 2026

(54) DIRECT-INJECT DISPOSAL SYSTEMS

(71) Applicant: Kohler Co., Kohler, WI (US)

(72) Inventors: Todd Leonhard, Sheboygan, WI (US); Jason Miller, Plymouth, WI (US); Kenneth Kapal, Sheboygan, WI (US); Erich Slothower, Kohler, WI (US); Pete Kajuch, Milwaukee, WI (US); Andrew Wasz, Kohler, WI (US); Eder Perez, Kohler, WI (US); Margaret Mazz, Kohler, WI (US); Evan Grybush, Belgium, WI (US); Matthew Wegner, Sheboygan, WI (US); Niels Eilmus, Kohler, WI (US); Josh Hippert, Kohler, WI (US); Jonathan Bradley, Grafton, WI (US)

(73) Assignee: Kohler Co., Kohler, WI (US)

( * ) Notice: Subject to any disclaimer, the term of this patent is extended or adjusted under 35 U.S.C. 154(b) by 283 days.

(21) Appl. No.: 18/531,649

(22) Filed: Dec. 6, 2023

(65) Prior Publication Data

US 2024/0200316 A1 Jun. 20, 2024

Related U.S. Application Data

(60) Provisional application No. 63/387,431, filed on Dec. 14, 2022, provisional application No. 63/489,686, filed on Mar. 10, 2023.

(51) Int. Cl.
*E03C 1/266* (2006.01)
*A61L 2/183* (2026.01)
(Continued)

(52) U.S. Cl.
CPC ................ *A61L 2/26* (2013.01); *A61L 2/183* (2013.01); *B08B 9/00* (2013.01); *E03C 1/182* (2013.01);
(Continued)

(58) Field of Classification Search
CPC ....... B02C 18/0084–0092; E03C 1/048; E03C 1/126; E03C 1/181; E03C 1/266–2665;
(Continued)

(56) References Cited

U.S. PATENT DOCUMENTS 2,784,915 A * 3/1957 Gordon ................ E03C 1/2665 241/46.08
4,183,470 A * 1/1980 Hovartos ............. E03C 1/2665 241/46.11
(Continued)

FOREIGN PATENT DOCUMENTS

CN 110471358 * 11/2019 .......... E03C 1/2665
KR 20130025936 * 3/2013 .......... E03C 1/2665

*Primary Examiner* — David P Angwin
*Assistant Examiner* — Nicholas A Ros
(74) *Attorney, Agent, or Firm* — Husch Blackwell LLP

(57) ABSTRACT

A disposal system utilizing a direct injection of water for an amount of time to sufficiently sanitize a chamber of the disposal system. The disposal system includes a chamber coupled to a drain of a sink at a first end of the chamber, and to a drainpipe at a second end of the chamber. A cutting mechanism, such as a rotary cutting blade, is positioned within the chamber near a floor of the chamber. A fluid-injection unit, such as a flange attachment, coupled to the first end of the chamber and the drain of the sink, includes a plurality of nozzles for introducing a fluid in a variety of streams in different directions to reach substantially an entirety of the chamber. The flange attachment can also include a water line attachment for connecting to a water line, with an optional ozone generator upstream from the disposal system.

16 Claims, 8 Drawing Sheets

(51) Int. Cl.
*A61L 2/26* (2006.01)
*B08B 9/00* (2006.01)
*E03C 1/182* (2006.01)

(52) U.S. Cl.
CPC ......... *E03C 1/2665* (2013.01); *A61L 2202/11* (2013.01); *A61L 2202/14* (2013.01); *A61L 2202/15* (2013.01); *A61L 2202/17* (2013.01)

(58) Field of Classification Search
CPC ........... E03C 2201/40; E03D 2009/028; E03D 2009/002; E03D 2009/005
See application file for complete search history.

(56) References Cited

U.S. PATENT DOCUMENTS

| | | | | |
|---|---|---|---|---|
| 5,249,749 | A * | 10/1993 | Krebsbach | E03C 1/2665 241/46.016 |
| 5,308,000 | A * | 5/1994 | Riley | B02C 25/00 241/35 |
| 6,719,228 | B2 * | 4/2004 | Berger | E03C 1/2665 241/46.016 |
| 7,100,850 | B2 * | 9/2006 | Farmerie | E03C 1/2665 241/46.016 |
| 9,506,231 | B2 * | 11/2016 | Gormley | B02C 18/0084 |
| 9,696,728 | B2 * | 7/2017 | Gormley | G05D 7/0635 |
| 10,471,438 | B2 * | 11/2019 | Chavez | B02C 18/12 |
| 11,512,459 | B2 * | 11/2022 | Bohlen | E03C 1/26 |
| 12,442,166 | B2 | 10/2025 | Eilmus et al. | |
| 2022/0364343 | A1 | 11/2022 | Eilmus et al. | |
| 2023/0064960 | A1 * | 3/2023 | Chen | E03C 1/2665 |

* cited by examiner

DIRECT-INJECT DISPOSAL SYSTEMS

CROSS-REFERENCE TO RELATED APPLICATIONS

The present disclosure claims priority to U.S. Provisional Application No. 63/387,431, filed Dec. 14, 2022, and U.S. Provisional Application No. 63/489,686, filed Mar. 10, 2023, the complete disclosures of which are incorporated herein by reference.

TECHNICAL FIELD

The present disclosure relates generally to in-sink disposals, and more particularly to self-cleaning direct-inject garbage disposals for use in retail, commercial, and industrial kitchen environments and the like.

BACKGROUND

Generally speaking, sinks are vessels configured for dispensing and draining water in a kitchen environment or washroom environment. A sink typically includes a faucet or other water-delivery device located proximate a basin of the sink, and a drainpipe is coupled to the basin to remove unwanted water (e.g., wastewater). In some sinks, a disposal system, such as a garbage-disposal system, is coupled between the basin and the drainpipe. For instance, the disposal system can include a motorized grinding mechanism, such as a blade, housed within a chamber of the disposal system. The blade can be activated to cut up, grind, break down, or otherwise pulverize any non-liquid food or other waste items that have been rinsed down the drain and into the chamber. Typically, water from the faucet is run simultaneously to guide the waste into the drainpipe, to keep the chamber clear from debris, and to subsequently flush the waste from the disposal. In such examples, however, the faucet must be manually activated by a user, i.e., independently from the disposal system.

Disposal systems can often produce unwanted odors and waste buildup, e.g., when waste is caught in the grinding mechanism or corners of the chamber without being rinsed out. There remains a need for a self-cleaning, sanitizing, and deodorizing disposal system that reduces unwanted buildup and odors.

SUMMARY

Examples of the present disclosure include a disposal system utilizing a direct injection of water, and optionally ozonated water, for a predetermined (or user-directed) amount of time to sufficiently sanitize a chamber of the disposal system.

In a non-limiting example, a disposal system can include a chamber fluidly couplable to a drain of a sink at a first end of the chamber, and connectable to a drainpipe at a second end of the chamber. A cutting mechanism, such as a rotary cutting blade, is positioned within the chamber near a floor of the chamber. The cutting mechanism is motorized, and can be activated by a user either remotely or by a switch, button, or other activation device. A flange attachment, coupled to the first end of the chamber and the drain of the sink, includes a plurality of nozzles for introducing a fluid in a variety of streams in different directions to reach substantially an entirety of the chamber. The flange attachment can also include a water line attachment for connecting to a water line, with an optional ozone generator upstream from the disposal system.

In non-limiting examples, water from the water line optionally passes through the ozone generator to produce ozonated water that enters into the disposal system via the flange attachment. For example, the ozonated water can have an ozone concentration of from about 0.001 parts per million (PPM) to about 0.5 PPM, and more specifically, from about 0.01 PPM to about 0.2 PPM. The flange attachment then introduces the ozonated water into the chamber. The plurality of nozzles, e.g., in the form of baffles, directly injects the ozonated water into chamber as a plurality of differently-oriented streams, so as to clean and sanitize substantially the entirety of the chamber in order to reduce unwanted odor and waste buildup. The direct injection of fluid from the flange attachment enables the disposal system to function without requiring that the faucet be run simultaneously, thereby greatly simplifying its use.

In non-limiting examples, the disposal system can include a smart sensor, as described in U.S. Pat. App. Pub. No. 2022/0364343, filed May 6, 2022, and entitled “Sink System and Components,” incorporated herein by reference in its entirety, which enables a user to run the disposal on automated cycles, such that the user does not need to be present to manually deactivate the disposal system. In non-limiting examples, the disposal system can include a smart manifold system including a relay to connect and disconnect a power supply for the disposal system.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Figure 1:
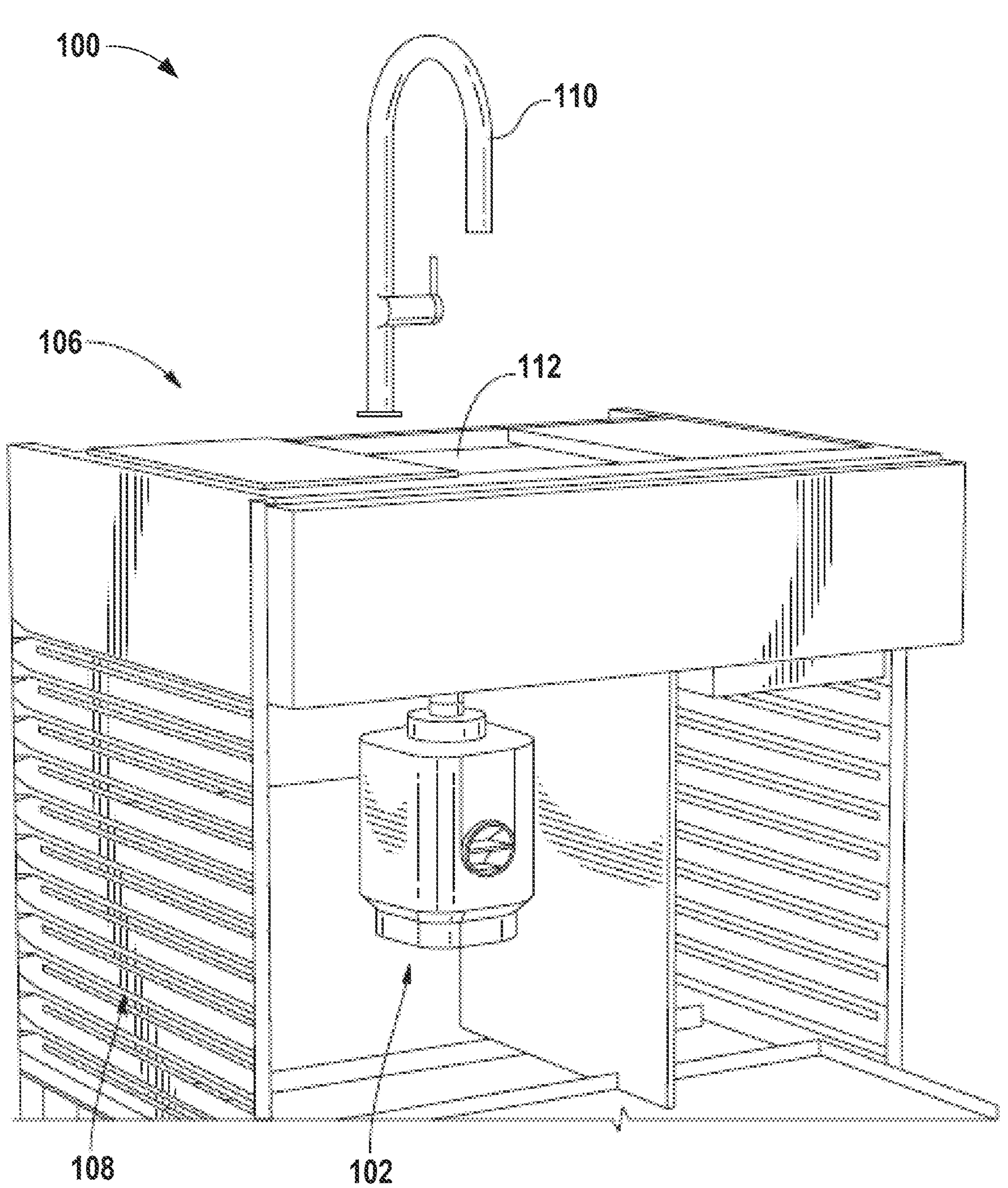
FIG. 1 is a perspective view of a sink system in general.
Figure 2:
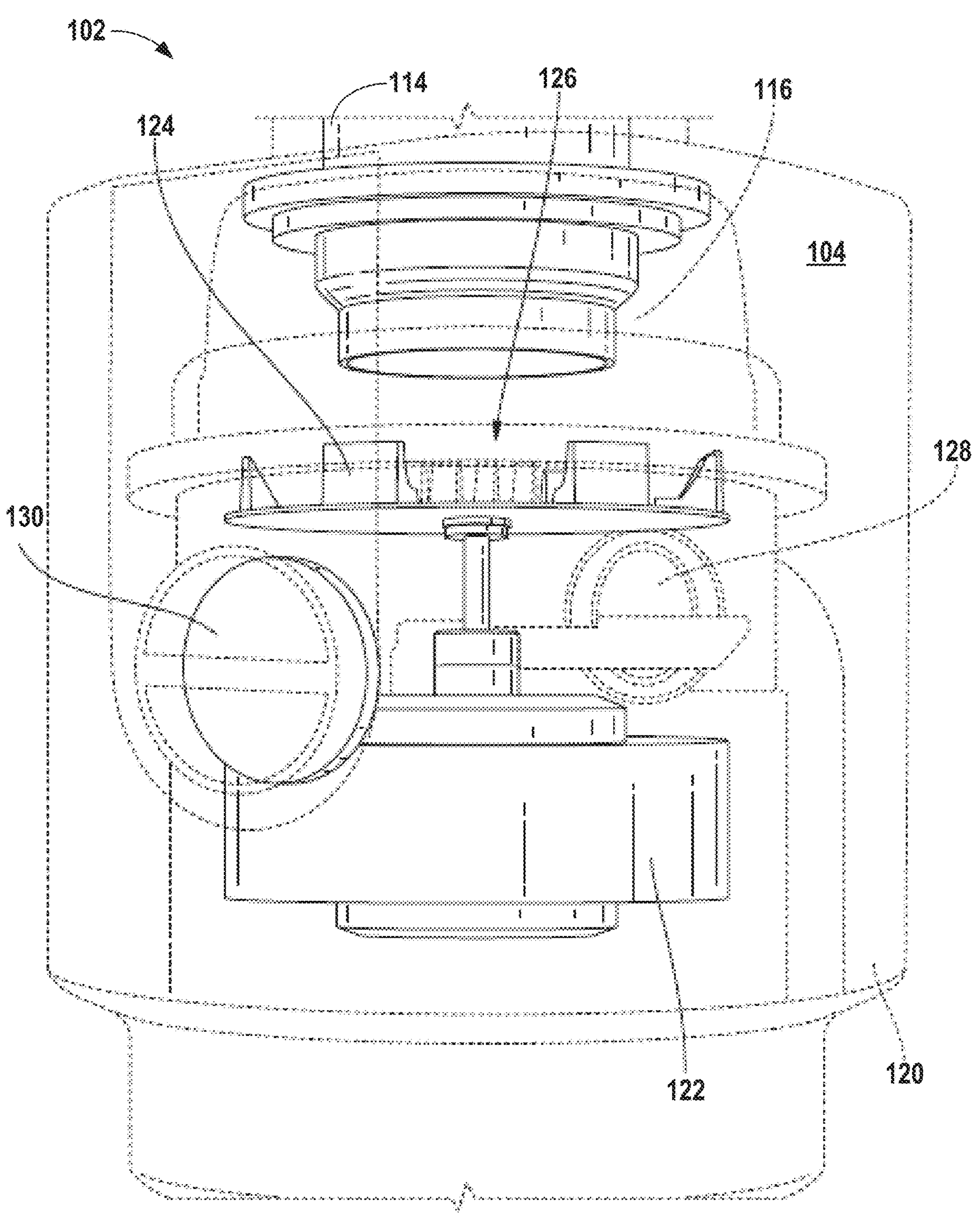
FIG. 2 is a schematic view of an example disposal system for the sink system of FIG. 1.

FIG. 1 is a perspective view of a sink system 100 that includes a waste-disposal system 102, and FIG. 2 is a schematic view of an example of the waste-disposal system 102 of FIG. 1. As shown in FIGS. 1 and 2, disposal system 102 can be or can include a direct-inject waste-disposal unit 104 configured to dispose of food or other kitchen waste, according to some examples. Sink system 100 can include a sink module 106 and an optional cabinet module 108. For instance, sink module 106 may be configured removably couple on top of cabinet module 108. Sink module 106 may be further configured to receive a material (e.g., fluid, waste, food, etc.) from a faucet 110, via a sink basin 112. The faucet 110 may be positioned proximate and on top of sink module 106. By way of example, a user can actuate the faucet 110 between an "on" position and an "off" position such that the faucet 110 selectively outputs material. Sink basin(s) 112 is configured to receive a flow of liquid and/or waste and deliver the flow to a drain opening 114. In some examples, drain opening 114 is fluidly coupled to disposal system 102. For example, drain opening 114 may be fluidly coupled with at least one of the inlets 116 of disposal system 102.

Figure 5:
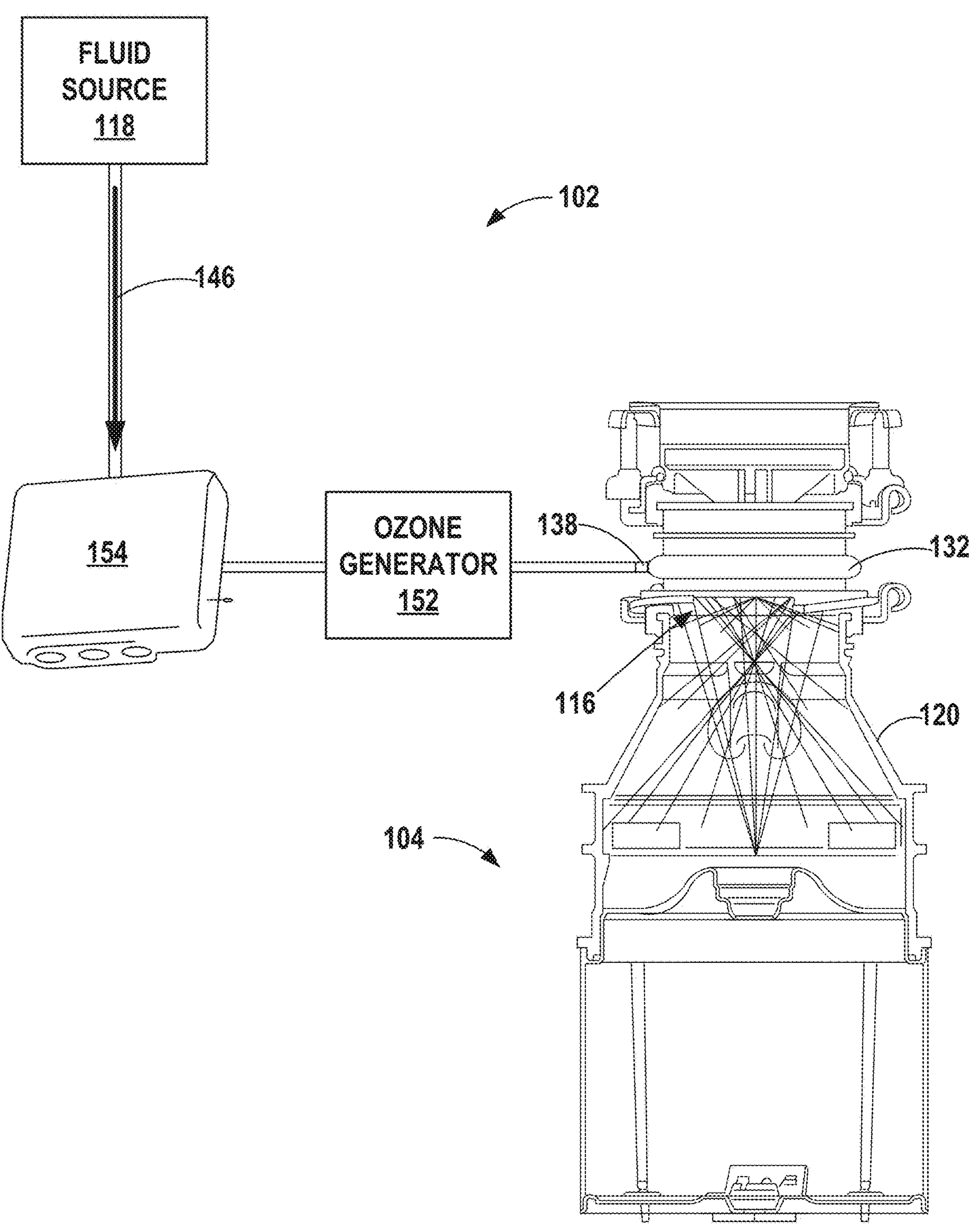
FIG. 5 depicts another example disposal system of the sink system of FIG. 1 including a direct-inject assembly coupled thereto and optional ozone generator assembly, according to an example.

In some examples, such as the example shown in FIG. 5, disposal system 102 includes at least one first fluid source 118 fluidly coupled with waste-disposal unit 104. The first fluid source 118 may direct fluid (e.g., ozonated or treated water) to an inlet 116 of the waste-disposal unit 104. For example, the inlet 116 may be a conduit, pipe, tube, or the like, configured to import a material into waste-disposal unit 104.

As shown in FIG. 2, waste-disposal unit 104 may include a body 120. For example, body 120 may be an exterior housing, casing, or the like that encloses the internal components of disposal unit 104. Body 120 of disposal unit 104 retains at least one power generator 122 (e.g., motors, gearboxes, turbines, etc.). Generator 122 is operably coupled to at least one grinding element 124 (e.g., blade, serrated projection, etc.) to facilitate breaking down and disposing waste.

Body 120 of disposal unit 104 defines main chamber 126. For example, main chamber 126 may be a volume within body 120 of disposal unit 104 in which fluid and waste interact with grinding element(s) 124. Disposal unit 104 further includes or defines at least one outlet 128 through which to expel fluid, food, and/or other waste from disposal unit 104. For instance, outlet 128 may be fluidly coupled to a sewer line.

In some examples, waste-disposal system 102 includes means for cleaning disposal-unit 104. For example, disposal system 102 may include a cleaner 130, such as a mechanical cleaner and/or chemical cleaner (e.g., soap, fragrance, etc.), configured to clean disposal unit 104 and reduce odor associated with system 102. Cleaner 130 may be provided to disposal unit 104 in various ways. For instance, a chemical cleaner 130 may be provided into body 120 via inlet(s) 116, e.g., from a cleaner source external to body 120. Chemical cleaner 130 may then be combined with liquid, air, or another component to activate (e.g., release chemicals, form bubbles, form ozone, etc.) cleaning of the interior of body 120. Additionally or alternatively, cleaner 130 may be internally disposed within body 120, e.g., in main chamber 126. In some examples, a user can control how waste-disposal system 102 utilizes cleaner 130. For instance, disposal system 102 may be configured for the user to manually install (e.g., fill, refill, load, unload, etc.) chemical cleaner 130 as desired.

Figure 3:
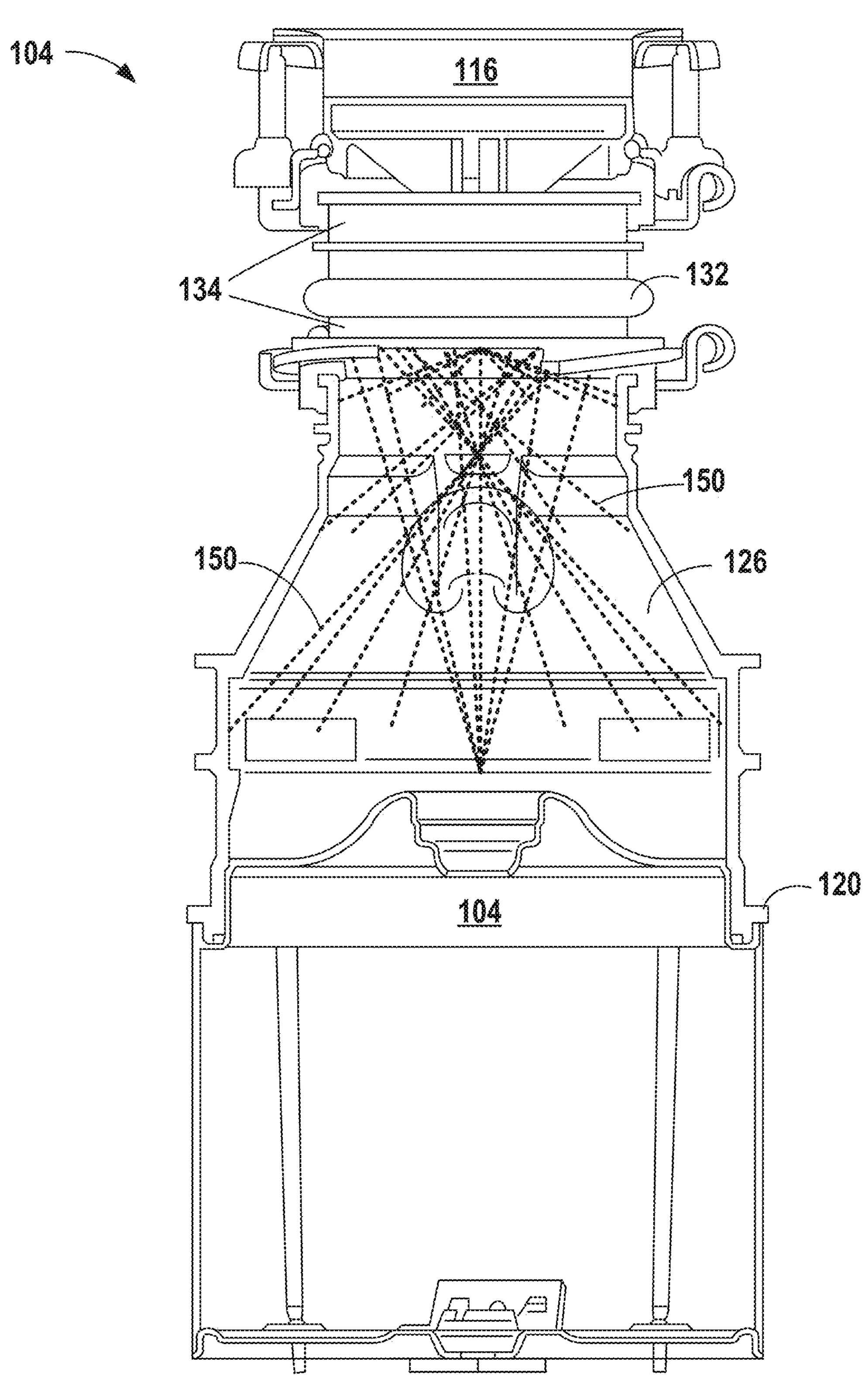
FIG. 3 is an elevational, cross-sectional view of the disposal system of FIG. 2 including a direct-inject assembly coupled thereto, according to an example.
Figure 4:
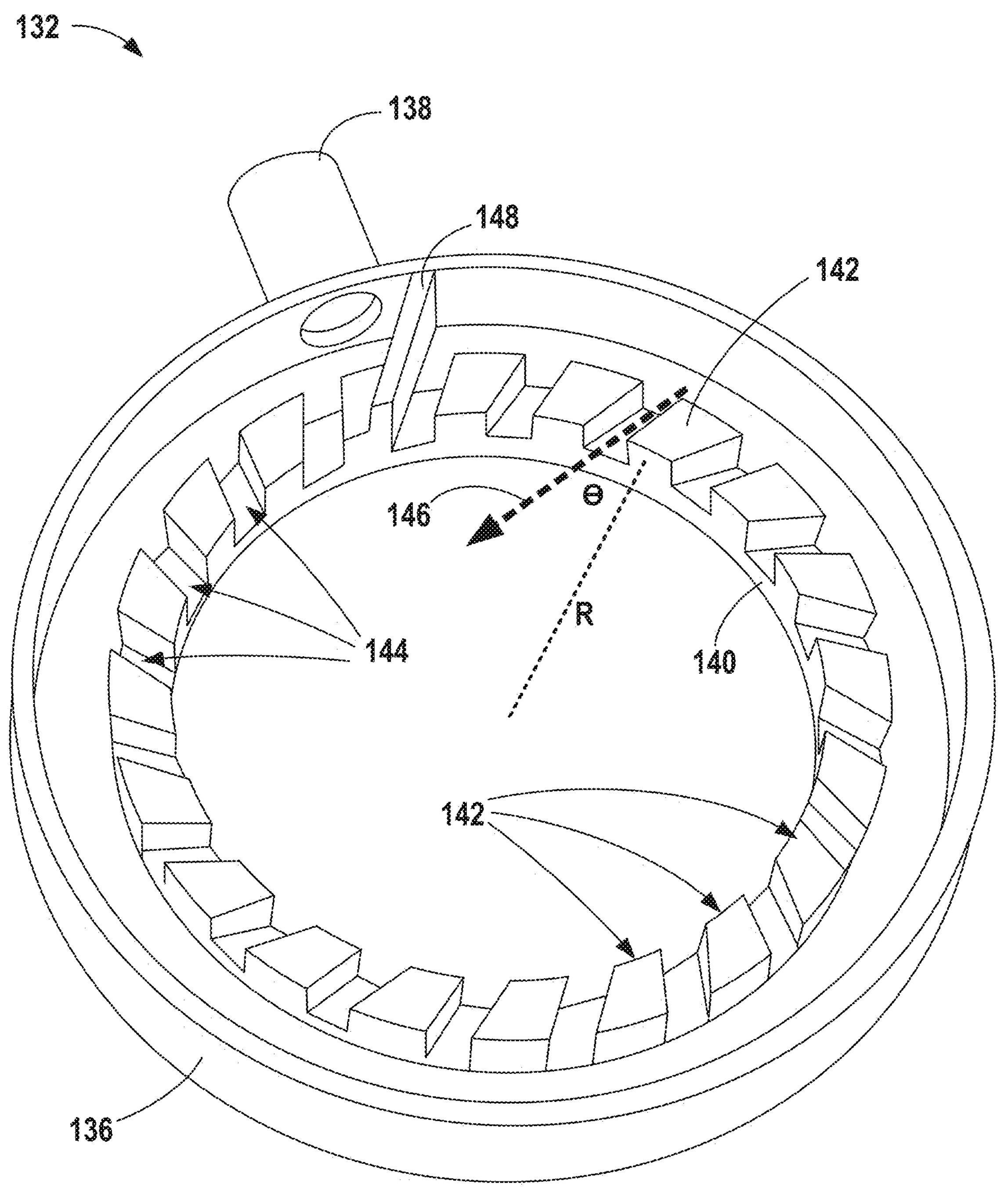
FIG. 4 is a top perspective view of a direct-inject ring unit including a modular flange with nozzles, according to an example.

As shown in FIGS. 3 and 4, waste-disposal unit 104 can include a fluid-injection unit 132 in the form of a modular flange attachment coupled between inlet 116 and body 120. Unit 132 can be removably coupled in-line (e.g., defining a common fluid pathway) with connector flange(s) 134 via threading, clamping, welding, or other suitable coupling mechanism. In another example unit 132 connects inline or into existing flange to disposal connections. As shown in FIG. 4, fluid-injection unit 132 can have an outer wall 136, e.g., in the shape of a ring, and can further include a fluid inlet/nozzle fitting 138 for coupling to fluid source 118 (FIG. 5), such as by press fit (e.g., friction retention) into or over nozzle fitting 138, by threaded engagement, by mechanical fasteners, or any combination or the above. Fluid-injection unit 132 can further define an inner surface 140 that defines a plurality of vertical protrusions or baffles 142, which themselves define a plurality of nozzles 144 therebetween. Nozzles 144 are oriented at angles "θ" relative to a radius "R" defined by circular inner surface 140 in order to deliver a fluid 146 into body 120 at angle θ. In some examples, fluid-injection unit 132 includes a barrier wall 148 proximate fluid inlet 138, which forces fluid 146 to flow in a particular direction relative to outer wall 136, e.g., either clockwise, or counterclockwise as depicted in the example shown in FIG. 4. This configuration of nozzles 144 allows ozonated water 146 to be delivered in a variety of intersecting streams 150 (FIG. 3) at different orientations to increase surface-area contact and sanitation of an interior of body 120. The ozonated spray pattern can also provide spray of the underside of the garbage disposer' spray guard when assembled to remove unwanted debris and bacteria.

FIG. 5 is a conceptual diagram of waste-disposal system 102 of FIG. 1. As referenced above, waste-disposal system 102 includes a fluid source 118 configured to provide a fluid 146 (e.g., water) to inlet 116 of disposal unit 104, via fluid inlet 138 of fluid-injection unit 132. For instance, fluid source(s) 118 can provide body 120 of disposal unit 104 with "gray" water (e.g., recirculated, reused, or unfiltered water), "fresh" water (e.g., from a water-delivery system, pipelines, manifold, etc.), or any combination thereof.

In some examples, disposal system 102 further includes a solenoid assembly (not shown in FIG. 5) including at least one solenoid valve. The solenoid assembly can be configured to receive signals from associated sensors or actuators. For instance, a sensor may automatically transmit a signal to the solenoid assembly in response to a certain condition, such as in response to detecting a user (e.g., a user's hand or foot), a weight of waste disposed within chamber 126, or the like. Additionally or alternatively, a user can manually actuate an actuator configured to transmit the signal to the solenoid assembly. In response, the solenoid assembly then causes a diaphragm or valve to open, thereby allowing water 146 or another fluid to flow into disposal unit 104.

In some examples, disposal system 102 includes a backflow prevention assembly (not shown) including a vacuum breaker or other backflow preventer to relieve unwanted vacuum which may develop in the disposal housing and to prevent backflow in the system. The backflow prevention assembly can be housed either below deck or above deck and at the appropriate level depending on code requirements.

In some examples, fluid source 118 directs fluid 146 through an ozone generator 152, in which ozone is generated within water 146 (e.g., at a concentration of about 0.001 parts-per-million (PPM) to about 0.5 PPM, and more specifically from about 0.01 PPM to about 0.2 PPM). The resulting ozonated water is then directed into disposal unit 104 via fluid inlet 1038 and nozzles 144 of fluid-injection unit 132. The ozonated water rinses, sanitizes, and deodorizes the interior of main chamber 126. Optional other chemical components 130 (FIG. 2), e.g. soaps, disinfectants, aromatics, and/or other substances to assist in disposing of waste, can also be added to the water 146, either upstream from, downstream from, or within ozone generator 152, or any suitable combination thereof.

Fluid source 118 may be directly fluidly coupled to disposal unit 104 such that disposal system 102 may operate without requiring an additional outside fluid source, such as fluid from faucet 110 (FIG. 1), and in some examples, even while no fluid is present within basin 112 of sink module 106. For instance, waste may be expelled from the basin 112 through the drain opening to the garbage disposal 102. In such examples, disposal unit 102 is configured to "automatically" break down and dispose of waste, i.e., without requiring a user to manually actuate faucet 110.

In some examples, waste-disposal system 102 includes an electronic or "smart" manifold 154 configured to control and operate disposal unit 104 as well as couple the fluid source 118, such as a hot water line, a cold water inlet, a grey water line, and can include one or more mixer valves. Manifold 154 can include its own power source, e.g., distinct from a power source of disposal unit 104, and a relay to activate and deactivate disposal unit 104, which is coupled to a separate circuit. For example, manifold 154 can include a 3-prong plug and relay to supply power to disposal unit 104 in place of an electrical switch or an air switch. In other examples, an electrical switch or an air switch can supply power to disposal unit 104.

In some examples, manifold 154 can include an integrated power monitor configured to measure electrical current to determine a "loaded" consumption and an "unloaded" consumption of the motor 122 (FIG. 2), thereby indicating when motor 122 is actively grinding waste debris. The integrated power monitoring can be combined with run-cycle timing to improve the elimination of waste from disposal unit 104. As referenced above, solenoid 154 can provide direct-inject ozonated water (or another fluid 146) to both activate and flush disposal unit 104 without running faucet 110.

Furthermore, smart manifold 154 can monitor usage timing and frequency, which can then be used to determine requirements for replacing, for instance, self-cleaning chemical(s) 130 (FIG. 2), a filter, and/or ozone generator 152. Internet-of-things (IOT) functionality of smart manifold 154 can also provide notifications to replace cleaning chemical 130, cycle-time programming, activation-safety protocols (e.g., to enable/disable quick-touch activation), error codes based on changes in electrical consumption of motor 122, and/or the like. Smart manifold 154 can further operate disposal system 102 automatically, allowing the user to leave the vicinity while the disposal system 102 runs until empty and cleans itself.

In some examples, disposal system 102 includes a controller communicably coupled to disposal unit 104 and one or more sensors (not shown), such as transducers, measurement devices, buttons, switches, user input devices, flow sensors, etc.), as detailed in U.S. Pat. App. Pub. No. 2022/0364343, incorporated in its entirety herein by reference. In particular, such arrangements are described with reference to FIGS. 3-1 through 3-8, and more particularly, FIGS. 3-4 through 3-8. In some examples, the controller may be internal to a component of waste-disposal system 102 and/or sink system 100, such as incorporated into a computing system for disposal system 102 and/or sink system 100. The controller may be incorporated as, or may be a component of, an application-specific integrated circuit (ASIC) for disposal system 102 and/or sink system 100. In some examples, the controller may be external to and communicably coupled [e.g., via various application programming interfaces (APIs)] to disposal system 102 and/or sink system 100. The controller may be configured to generate control signals for disposal system 102 based on user input to a control member.

Figure 6:
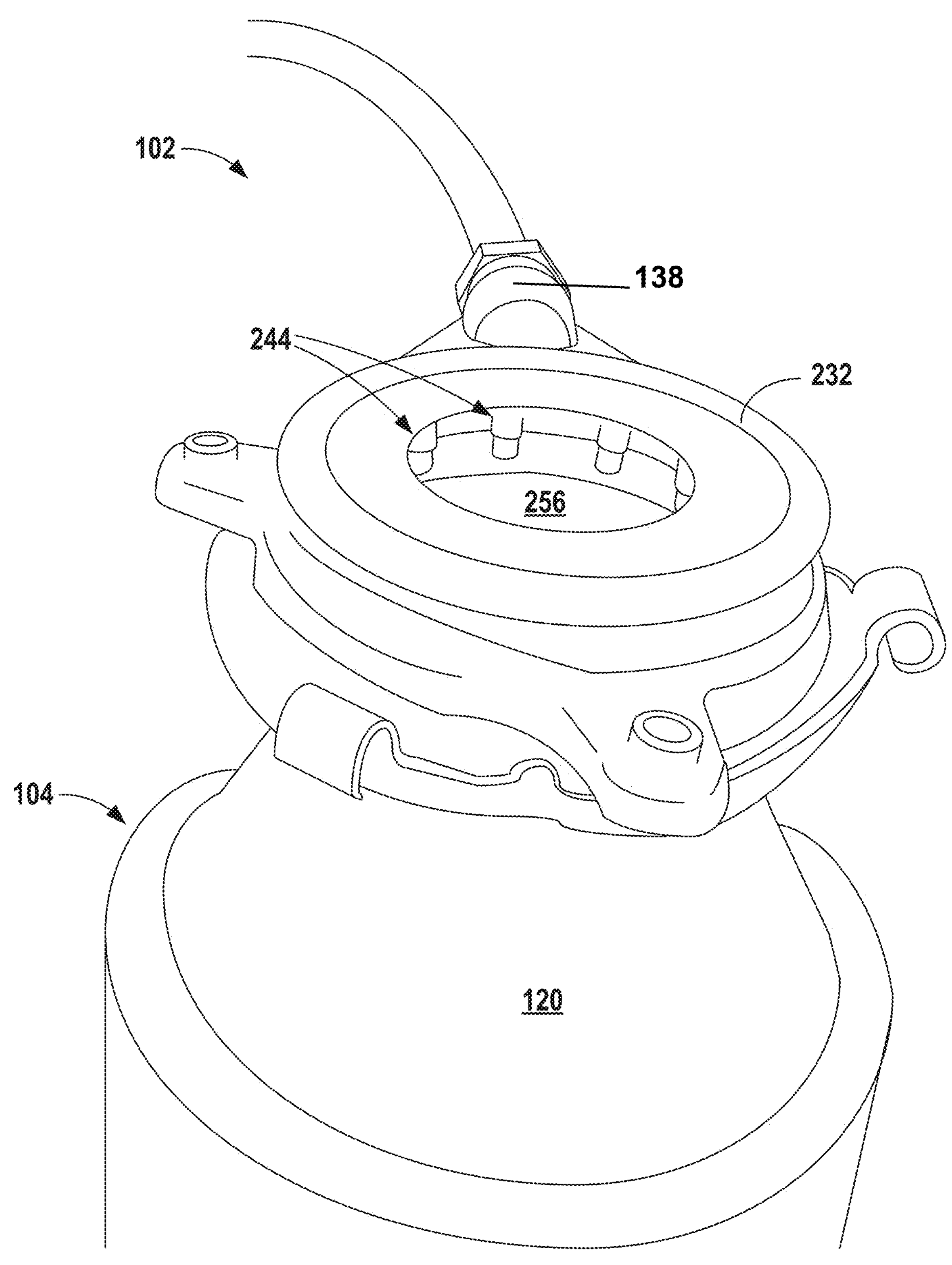
FIG. 6 depicts an example of the disposal system of FIG. 2, including a sandwich-type direct-inject ring unit assembly, according to an example.

FIG. 6 depicts another example of direct-inject waste-disposal system 102 and fluid-injection unit 232. In this example, fluid-injection unit 232 is a sandwich-type unit, in that it is configured to be "sandwiched" (e.g., removably coupled) between housing 120 of disposal unit 102 and an underside of sink basin 112 (FIG. 1). Similar to fluid-injection unit 132, fluid-injection unit 232 includes a plurality of nozzles 244 configured to inject fluid, such as tap water, gray water, or ozonated water, into an inner space 256 to help rinse and dispose of food waste as it descends into housing 120 and/or to clean housing 120. Similar to other examples, fluid injection unit 332 includes a fluid inlet/nozzle fitting 138 for coupling to fluid source, such as by press fit (e.g., friction retention) into or over nozzle fitting 138, by threaded engagement, by mechanical fasteners, or any combination or the above.

In some examples, fluid-injection unit 232 is operably coupled to an actuator of disposal unit 104, such that fluid-injection unit 232 is configured to run simultaneously when disposal unit 104 (e.g., grinding element 124) is actuated. In this way, a user does not need to manually run water from faucet 110 in order to operate disposal unit 104.

Figure 7:
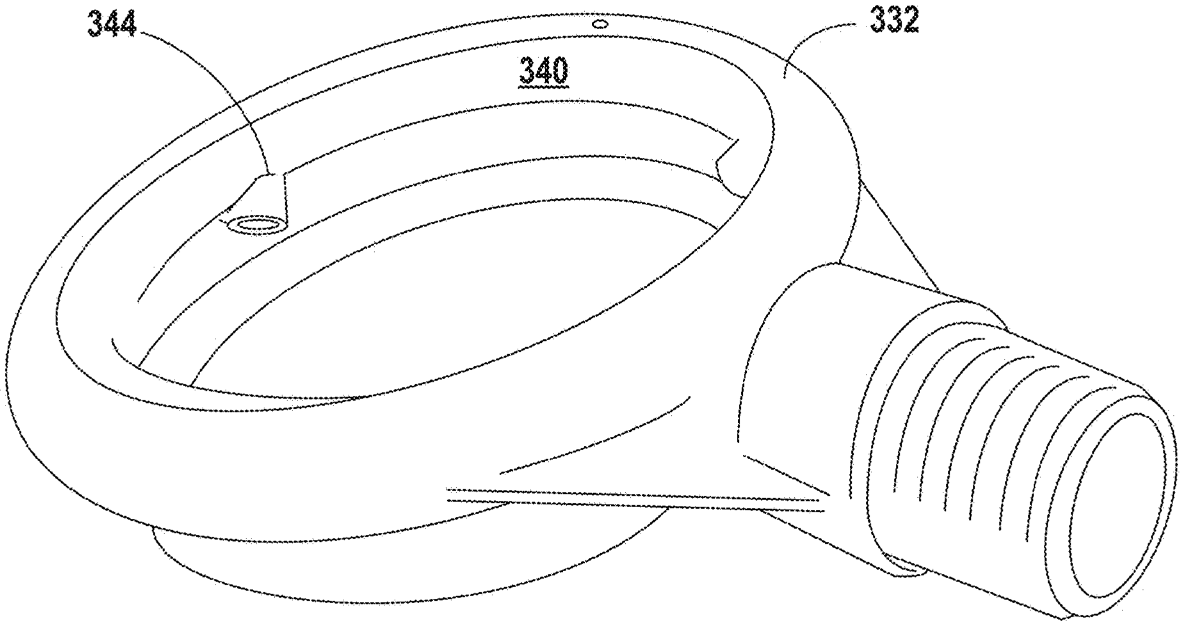
FIG. 7 depicts a direct-inject ring unit including a modular flange with nozzles, according to another example.

FIG. 7 depicts a fluid-injection unit 332, according to another example. In the example of FIG. 7, fluid-injection unit 332 includes about three (or more or less) fluid nozzles 344 distributed circumferentially about an inner surface 340. Nozzles 344 are oriented at angles relative to a radius of circular inner surface 340, so as to form a "vortex" type flow as water is injected through nozzles 344. In some examples, fluid-injection unit 332 may be formed from a material such as rubber such that unit 332 may be retained within a drain of sink basin 112 through friction. Fluid-injection unit 332 may also be sandwiched between a disposal unit and an underside of a sink basin. Similar to other examples, fluid injection unit 332 includes a fluid inlet/nozzle fitting 138 for coupling to fluid source, such as by press fit (e.g., friction retention) into or over nozzle fitting 138, by threaded engagement, by mechanical fasteners, or any combination or the above.

Figure 8:
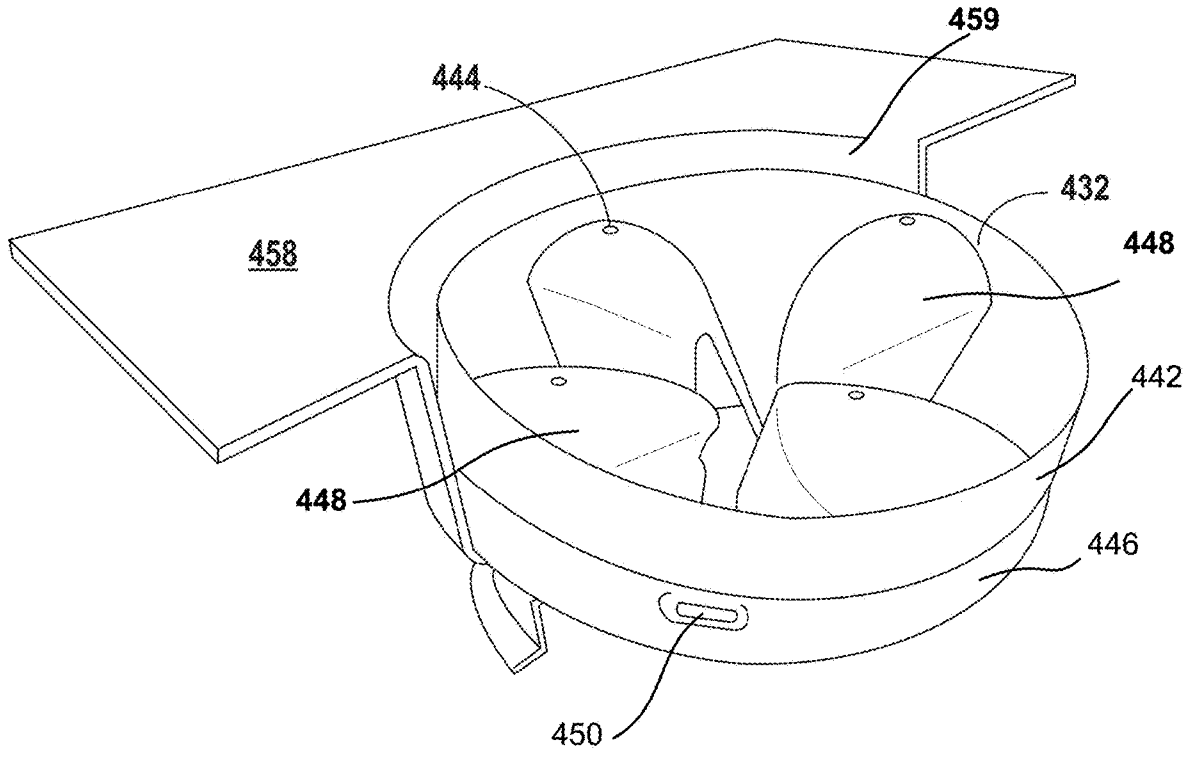
FIG. 8 is a perspective view of a drain splash guard to be used in combination with a direct-inject assembly, according to an example.

FIG. 8 depicts a splashguard unit 432, which can be used in combination with the fluid-injection unit 132 of FIG. 4, fluid-injection unit 232 of FIG. 6, or fluid-injection unit 332 of FIG. 7. Splashguard unit 432 is configured to fit within sink basin 458, e.g., underneath a circular drain flap (not shown) typically included with kitchen-sink units or within a drain, such as a seamless drain 459, of a sink basin 458. In some such examples, splashguard unit 432 includes a sidewall 442 terminating in an annular base portion 446 that includes structure defining a trench on its outer surface, and a plurality of inverted petals or drainage flanges 448 extending inwardly from the sidewall 442. Petals 448 can be tear-drop shaped or any of a variety of shapes that can prevent or reduce the exit of fluid from the waste disposal system. Apertures or nozzles 450 are defined within annular base portion 446 for introducing fluid towards an interior of the inverted petals 448. Nozzles may be equally spaced about base portion 446, or can be unequally spaced. One or more of petals 448 can further include structure defining one or more upward-facing nozzles 444 configured to help clean an underside of the circular drain flap, an area notorious for accumulating waste buildup over time.

As fluid enters the fluid-injection unit (not shown) and exits out its nozzles, as described in the examples above, it moves along the recessed base portion 446 of the splashguard unit 432 and through one or more apertures or nozzles 446 and along the underside of petals 448 to clean an underside of unit 432. The fluid then moves through optional nozzles 444 to an underside of the circular drain flap (if present) to clean or sanitize the underside.

In examples, the direct injection of fluid to the splash-guard 432 may be configured to clean, rinse, or otherwise sanitize the internal structures of the drain environment of the drain 104. In some examples, fluid flow through the fluid inlet stem 124 may be conducted automatically with the activation of a disposal system (i.e., without requiring the flow of liquid from the faucet), automatically via a digital valve, or manually via activation of the button, switch, or other actuator.

As utilized herein with respect to numerical ranges, the terms "approximately," "about," "substantially," and similar terms generally mean+/−10% of the disclosed values, unless specified otherwise. As utilized herein with respect to structural features (e.g., to describe shape, size, orientation, direction, relative position, etc.), the terms "approximately," "about," "substantially," and similar terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above.

It is important to note that any element disclosed in one embodiment may be incorporated or utilized with any other embodiment disclosed herein.

What is claimed is:

1. A fluid-injection unit for use with and coupleable to a waste disposal system, the fluid injection assembly comprising:

a structure having a fluid inlet on an outer surface thereof, the fluid inlet being coupleable to an external fluid source;

a plurality of vertical protrusions in an annular arrangement; and a plurality of nozzles each defined between adjacent vertical protrusions and each oriented toward a central axis of the structure and downward toward the waste disposal system, wherein the fluid injection unit is configured to direct fluid from the fluid inlet to the plurality of nozzles to create a plurality of intersecting fluid streams.

2. The fluid-injection unit of claim 1, wherein the structure comprises a ring removably couplable between a chamber of the waste disposal system and a drain opening of a sink basin.

3. The fluid-injection unit of claim 2, wherein the ring includes a first barrier wall proximal to the fluid inlet, the fluid-injection unit being configured such that fluid flow entering via the fluid inlet is forced in a particular direction relative to an outer wall of the ring.

4. A waste disposal system for use with a sink assembly including a basin and structure defining a drain opening, the waste disposal system comprising:

a waste disposal unit, comprising a chamber having at least a first end and a second end, wherein the first end of the first chamber is fluidly coupled to the drain opening and the second end is connected to an outlet, and a motorized cutting mechanism housed within the first chamber; and a fluid-injection unit disposed within or proximate the first end of the waste disposal unit, the direct injection assembly including a structure having:

a fluid inlet defined on an outer surface thereof, the fluid inlet being coupleable to a fluid source;

a plurality of vertical protrusions in an annular arrangement; and a plurality of nozzles each defined between adjacent vertical protrusions and each directed inwardly toward a center of the fluid-injection unit and downwardly toward an interior of the chamber, wherein the fluid-injection unit is configured to direct fluid received from the fluid inlet to the plurality of nozzles to allow a plurality of intersecting fluid streams to enter the chamber.

5. The waste disposal system of claim 4, wherein the fluid inlet comprises a stem, and wherein the fluid source is removably couplable to the stem.

6. The waste disposal system of claim 4, further comprising an ozone generator positioned between the fluid source and the fluid inlet, wherein the system is configured to direct fluid from the fluid source through the ozone generator, the ozone generator being configured to generate ozonated water for injection into the waste disposal unit.

7. The waste disposal system of claim 4, further comprising a cleaning agent repository in fluid communication with the structure, wherein the system is configured to direct a cleaning agent from the cleaning agent repository into the fluid for cleaning the chamber.

8. The waste disposal system of claim 4, further comprising a solenoid assembly having at least a first solenoid valve, wherein the solenoid assembly is configured to receive signals from associated sensors or actuators, and wherein, in response to received signals, the solenoid assembly causes the first solenoid valve to open and allow fluid to enter the direct injection assembly.

9. The waste disposal system of claim 4, further comprising a manifold configured to control and operate waste disposal unit, wherein the manifold includes an independent power source and a relay to activate and deactivate the waste disposal unit.

10. The waste disposal system of claim 9, wherein the manifold includes an integrated power monitor configured to measure electrical current to determine a loaded consumption and an unloaded consumption of the cutting mechanism, thereby indicating when the cutting mechanism is in active use.

11. The waste disposal system of claim 10, wherein the integrated power monitor is further configured to monitor run-cycle timing to enhance elimination of wastewater from the waste disposal unit.

12. The waste disposal system of claim 4, further comprising:

a splashguard configured to seat in the drain opening of the sink assembly, the splashguard comprising a sidewall, a base portion extending below a bottom edge of the sidewall, and a plurality of drainage flanges extending inwardly within a perimeter of the sidewall.

13. The waste disposal system of claim 12, wherein the base portion includes structure defining one or more apertures, and wherein the splashguard is configured such that at least a part of the fluid from the fluid injection unit is directed through the one or more apertures, and to an underside of the plurality of drainage flanges.

14. A sink assembly, comprising:

a basin comprising a floor and a plurality of sidewalls extending upwardly from the floor, the floor and the plurality of sidewalls defining a reservoir that is configured to receive fluid therein;

a faucet for dispensing a fluid therefrom;

a drain opening extending downwardly from the floor of the basin;

a waste disposal unit comprising a chamber having a cutting or pulverizing unit housed within the chamber, the chamber having at least a first end and a second end, wherein the first end of the first chamber is fluidly coupled to the drain opening; and a fluid-injection unit disposed within or proximate the first end of the waste disposal unit, the fluid-injection unit including:

a plurality of vertical protrusions in an annular arrangement; and a plurality of nozzles each defined between adjacent vertical protrusions and each directed inwardly toward a center of the fluid-injection unit and downwardly toward an interior of the first chamber, wherein the fluid-injection unit is configured to direct fluid received from an external fluid source coupled to the fluid-injection unit to the plurality of nozzles and into the chamber.

15. The sink assembly of claim 14, wherein the fluid-injection unit comprises a structure having a fluid inlet on an outer surface thereof, the fluid inlet being coupleable to an external fluid source, and wherein the plurality of nozzles is formed on an inner surface of the structure.

16. The sink assembly of claim 14, wherein the waste disposal unit is configured to be run when fluid is directed within the chamber via the fluid-injection unit, independent of whether the faucet is dispensing fluid therefrom.

* * * * *